(12) United States Patent
Wang

(10) Patent No.: US 12,023,270 B2
(45) Date of Patent: Jul. 2, 2024

(54) CERVICAL COLLAR

(71) Applicant: Yu-Chien Wang, Taichung (TW)

(72) Inventor: Yu-Chien Wang, Taichung (TW)

( * ) Notice: Subject to any disclaimer, the term of this patent is extended or adjusted under 35 U.S.C. 154(b) by 400 days.

(21) Appl. No.: 17/586,154

(22) Filed: Jan. 27, 2022

(65) Prior Publication Data

US 2023/0233354 A1    Jul. 27, 2023

(51) Int. Cl.
*A61F 5/05*    (2006.01)
*A61F 5/055*    (2006.01)

(52) U.S. Cl.
CPC .................................. *A61F 5/055* (2013.01)

(58) Field of Classification Search
CPC .. A61F 5/055; A61F 5/05883; A61F 5/05816; A61F 5/05858; A61F 2005/0197
See application file for complete search history.

(56) References Cited

U.S. PATENT DOCUMENTS

| 2008/0156332 A1 * | 7/2008 | Ray | A61F 5/055 128/845 |
| 2018/0000625 A1 * | 1/2018 | Wang | A61F 5/055 |

* cited by examiner

*Primary Examiner* — Camtu T Nguyen
(74) *Attorney, Agent, or Firm* — Muncy, Geissler, Olds & Lowe, P.C.

(57) ABSTRACT

A cervical collar is provided, including: a collar member; a chin support, movably disposed on the collar member; a connection member, movably disposed on the collar member, connected with the chin support; and an adjustment assembly, including an inner thread portion, a thread shaft and a knob, the inner thread portion being disposed on the connection member, the thread shaft being disposed on the collar member and rotatable about an axial direction, the inner thread portion and the thread shaft being screwed with each other, the knob being connected with the thread shaft on the axial direction and located outside an end of the collar member in the axial direction, wherein the thread shaft rotates to drive the inner thread portion to move in the axial direction.

9 Claims, 9 Drawing Sheets

CERVICAL COLLAR

BACKGROUND OF THE INVENTION

Field of the Invention

The present invention relates to a cervical collar.

Description of the Prior Art

A conventional cervical collar or neck brace is used to hold the injured cervical vertebra in position to reduce the burden and avoid secondary injuries caused by activities. However, in the conventional cervical collar or neck brace the relative position of the collar member and the chin support board cannot be adjusted according to various requirements, thus resulting in inconvenience in use. Therefore, an adjustable cervical collar or neck brace has been developed accordingly.

However, the adjustment mechanisms of the conventional cervical collar or neck brace are located on opposing sides, so the two adjustment mechanisms must be adjusted at the same time in order to adjust or locate the relative positions of the collar member and the chin support board. Moreover, it is difficult to synchronously adjust the adjustment mechanisms on both sides to the same height position. If the both sides of the conventional cervical collar or neck brace are not located in the same height position, it is easy to cause secondary injury.

The present invention is, therefore, arisen to obviate or at least mitigate the above-mentioned disadvantages.

SUMMARY OF THE INVENTION

The main object of the present invention is to provide a cervical collar which is easy, smooth and stable to adjust the position of a chin support.

To achieve the above and other objects, a cervical collar is provided, including: a collar member; a chin support, movably disposed on the collar member; a connection member, movably disposed on the collar member, connected with the chin support; and an adjustment assembly, including an inner thread portion, a thread shaft and a knob, the inner thread portion being disposed on the connection member, the thread shaft being disposed on the collar member and rotatable about an axial direction, the inner thread portion and the thread shaft being screwed with each other, the knob being connected with the thread shaft on the axial direction and located outside an end of the collar member in the axial direction, wherein the thread shaft rotates to drive the inner thread portion to move in the axial direction.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
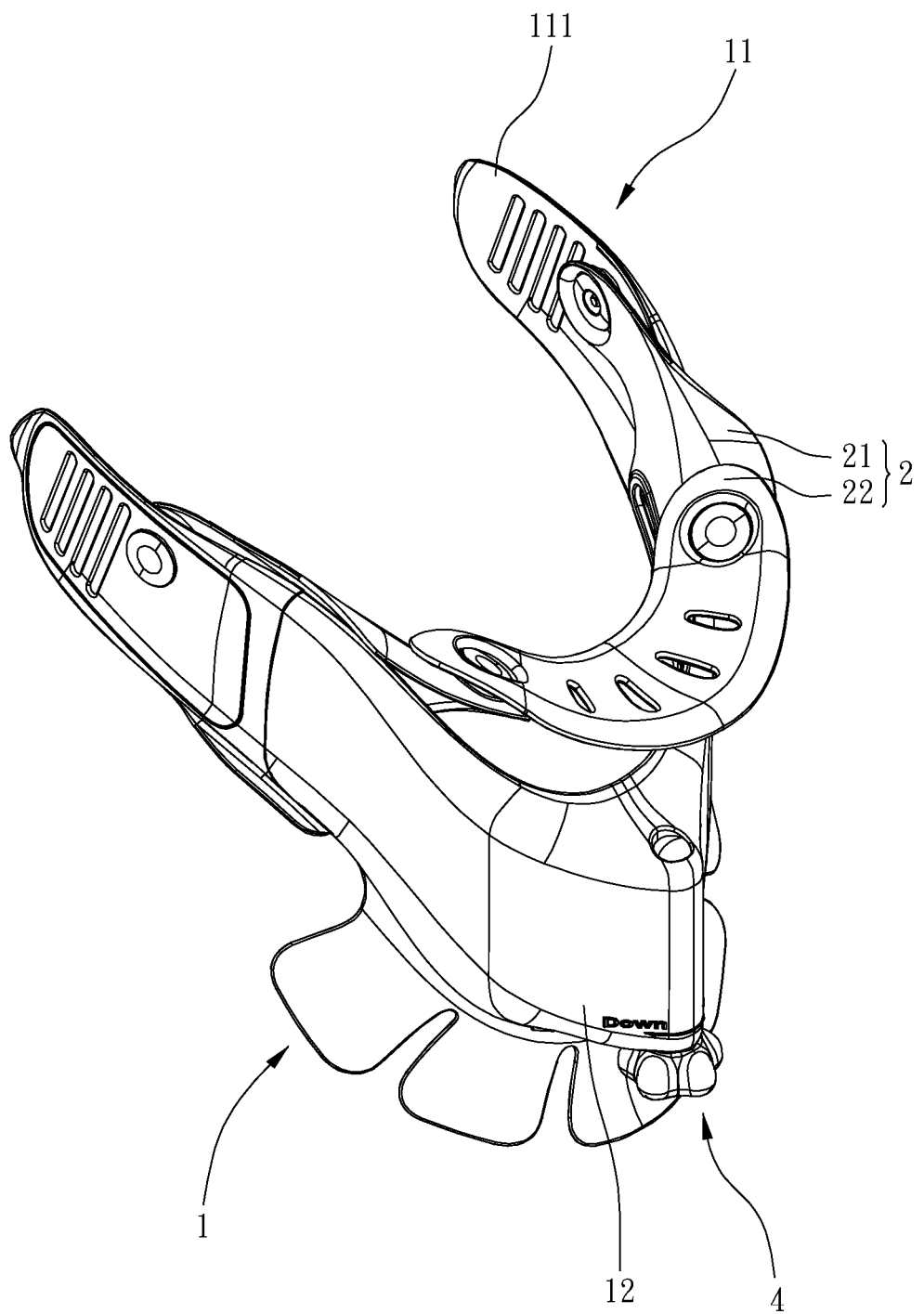
FIG. 1 is a stereogram of a preferable embodiment of the present invention.
Figure 2:
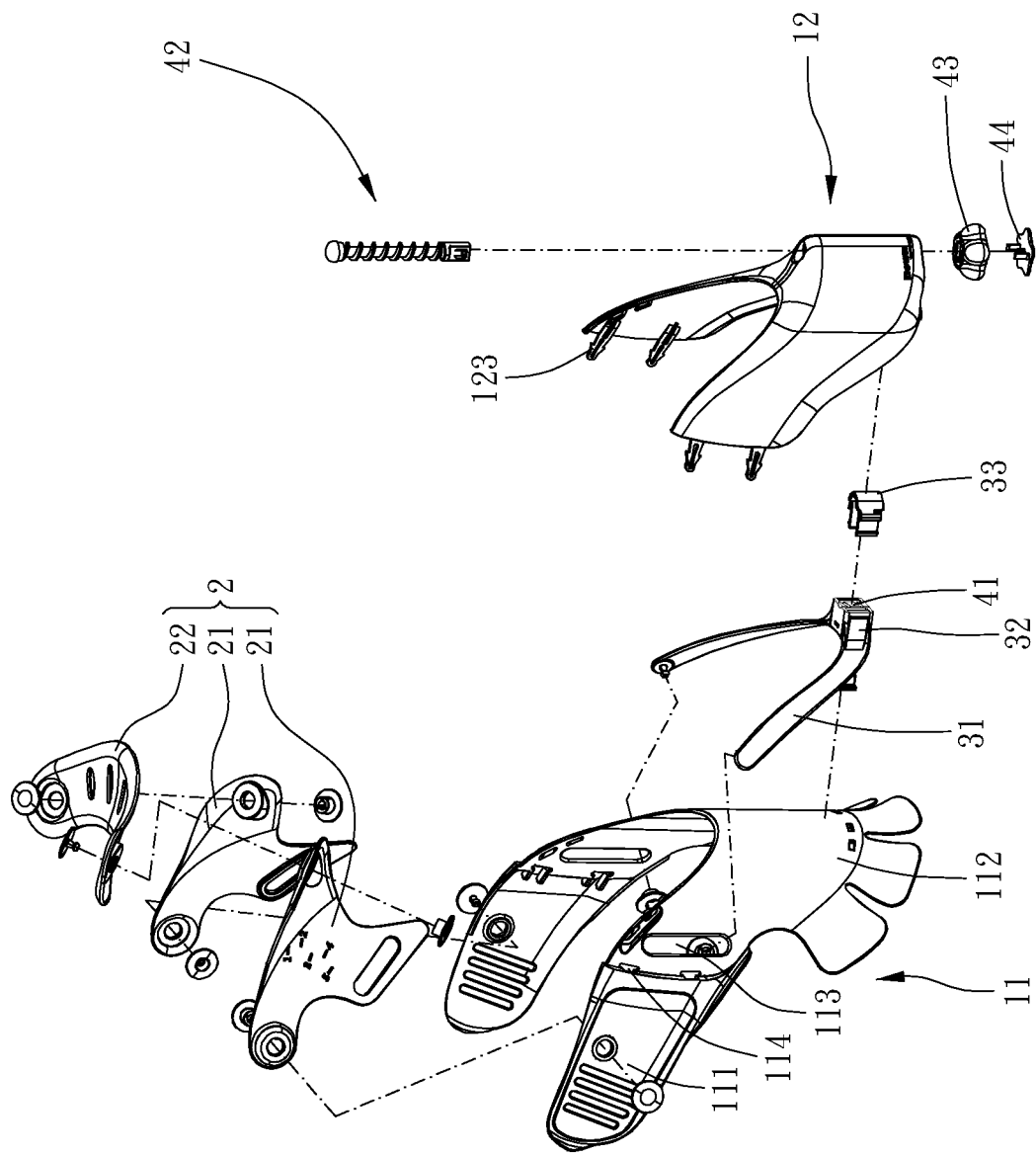
FIG. 2 is a breakdown drawing of a preferable embodiment of the present invention.
Figure 3:
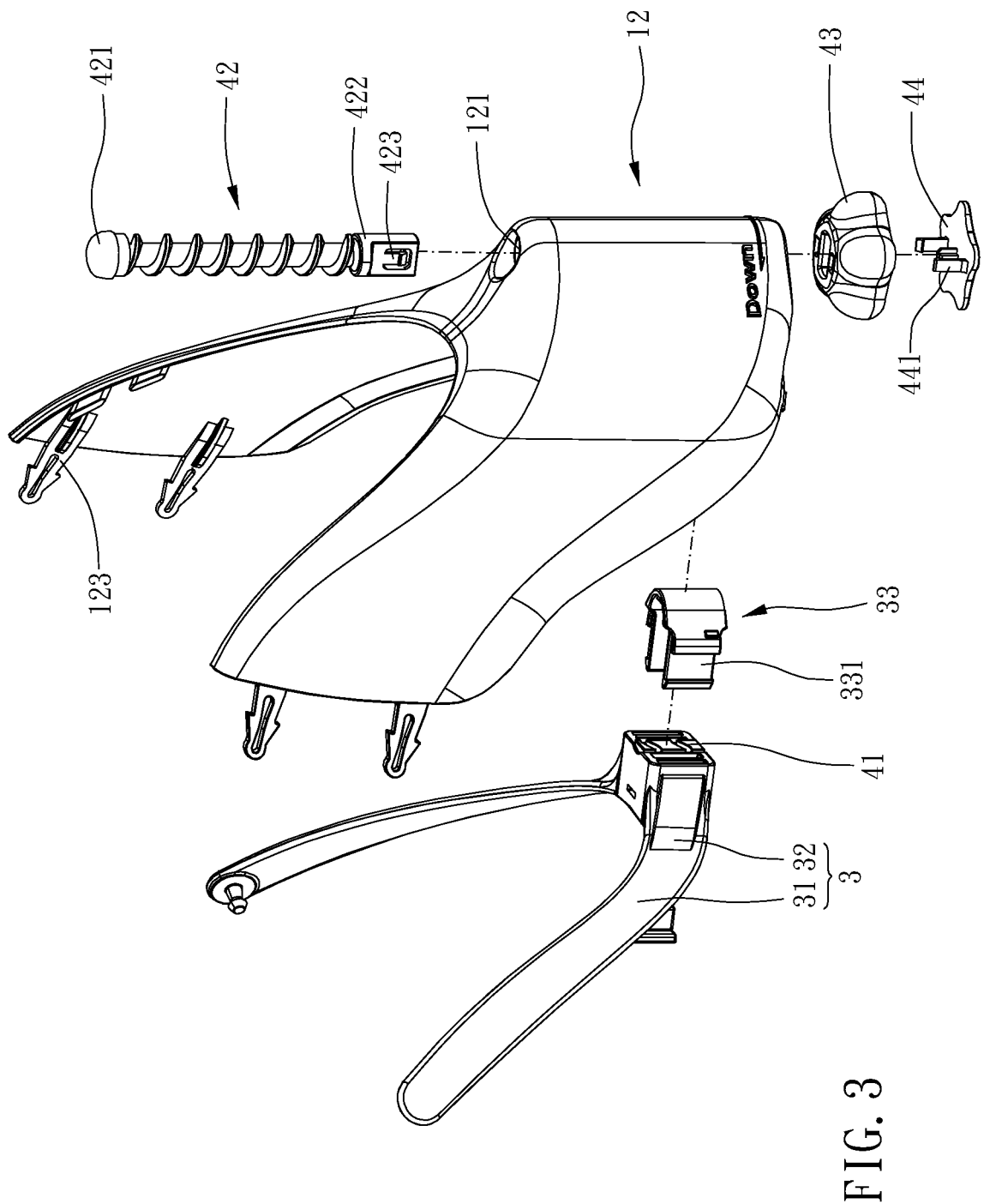
FIG. 3 is a partial enlargement of FIG. 2.
Figure 4:
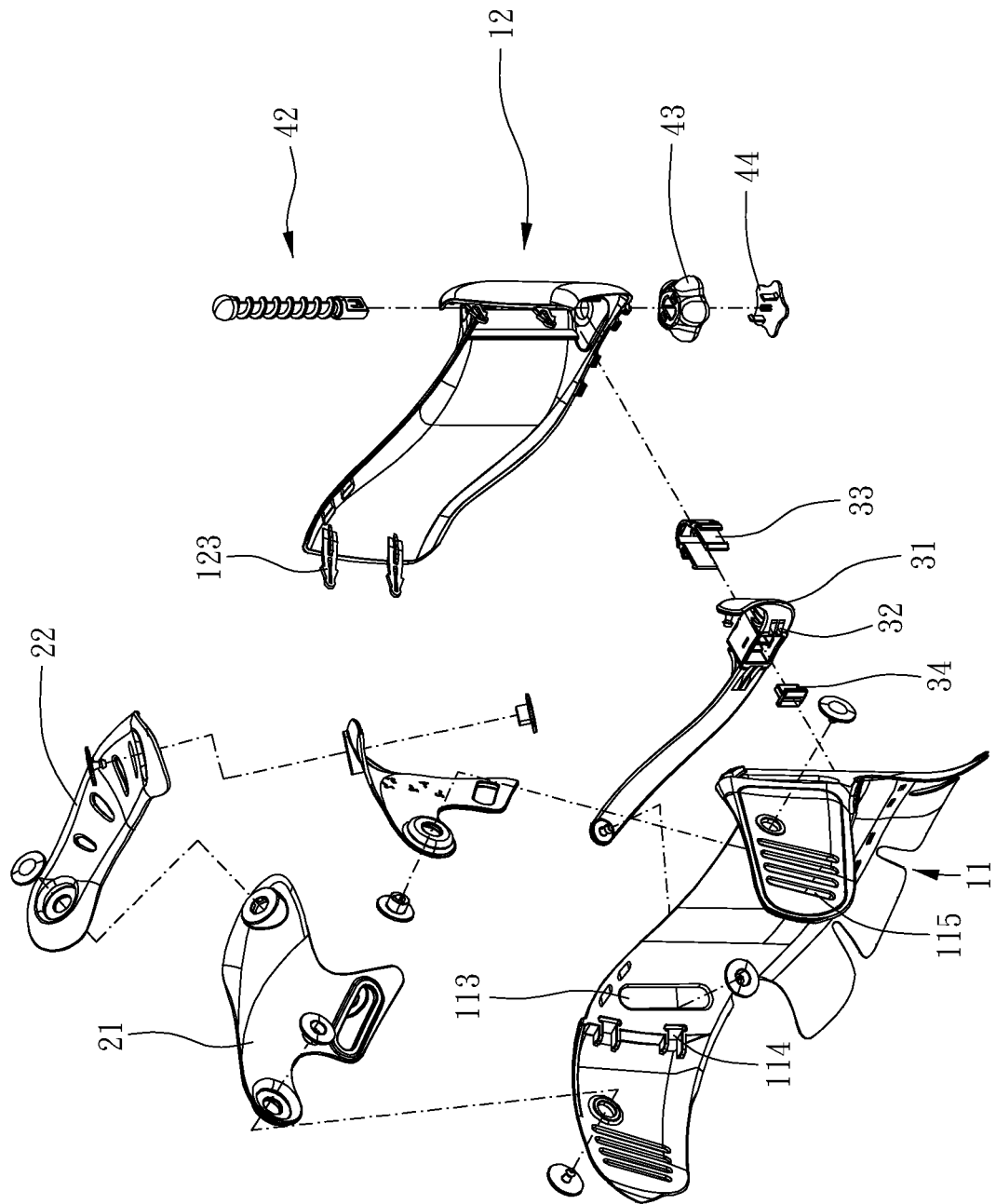
FIG. 4 is another breakdown drawing of a preferable embodiment of the present invention.
Figure 5:
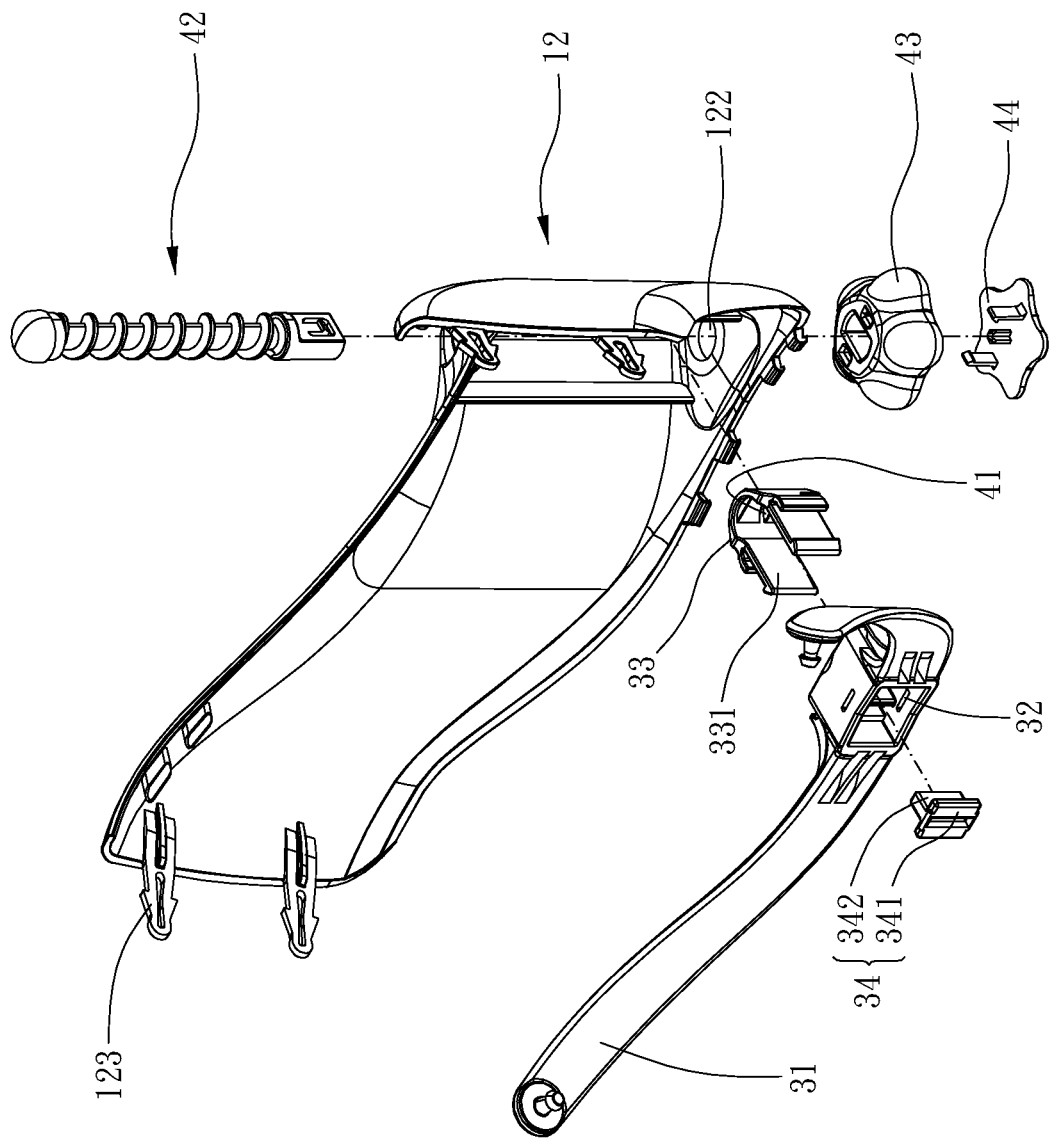
FIG. 5 is a partial enlargement of FIG. 4.

Please refer to FIGS. 1 to 9 for a preferable embodiment of the present invention. A cervical collar of the present invention includes a collar member 1, a chin support 2, a connection member 3 and an adjustment assembly 4.

The chin support 2 is movably disposed on the collar member 1, for supporting a chin of a user.

The connection member 3 is movably disposed on the collar member 1 and connected with the chin support 2.

The adjustment assembly 4 includes an inner thread portion 41, a thread shaft 42 and a knob 43, the inner thread portion 41 is disposed on the connection member 3, the thread shaft 42 is disposed on the collar member 1 and rotatable about an axial direction, the inner thread portion 41 and the thread shaft 42 are screwed with each other, and the knob 43 is connected with an end of the thread shaft 42 on the axial direction and located outside an end of the collar member 1 in the axial direction. Whereby, the thread shaft 42 rotates to drive the inner thread portion 41 to move in the axial direction.

Figure 6:
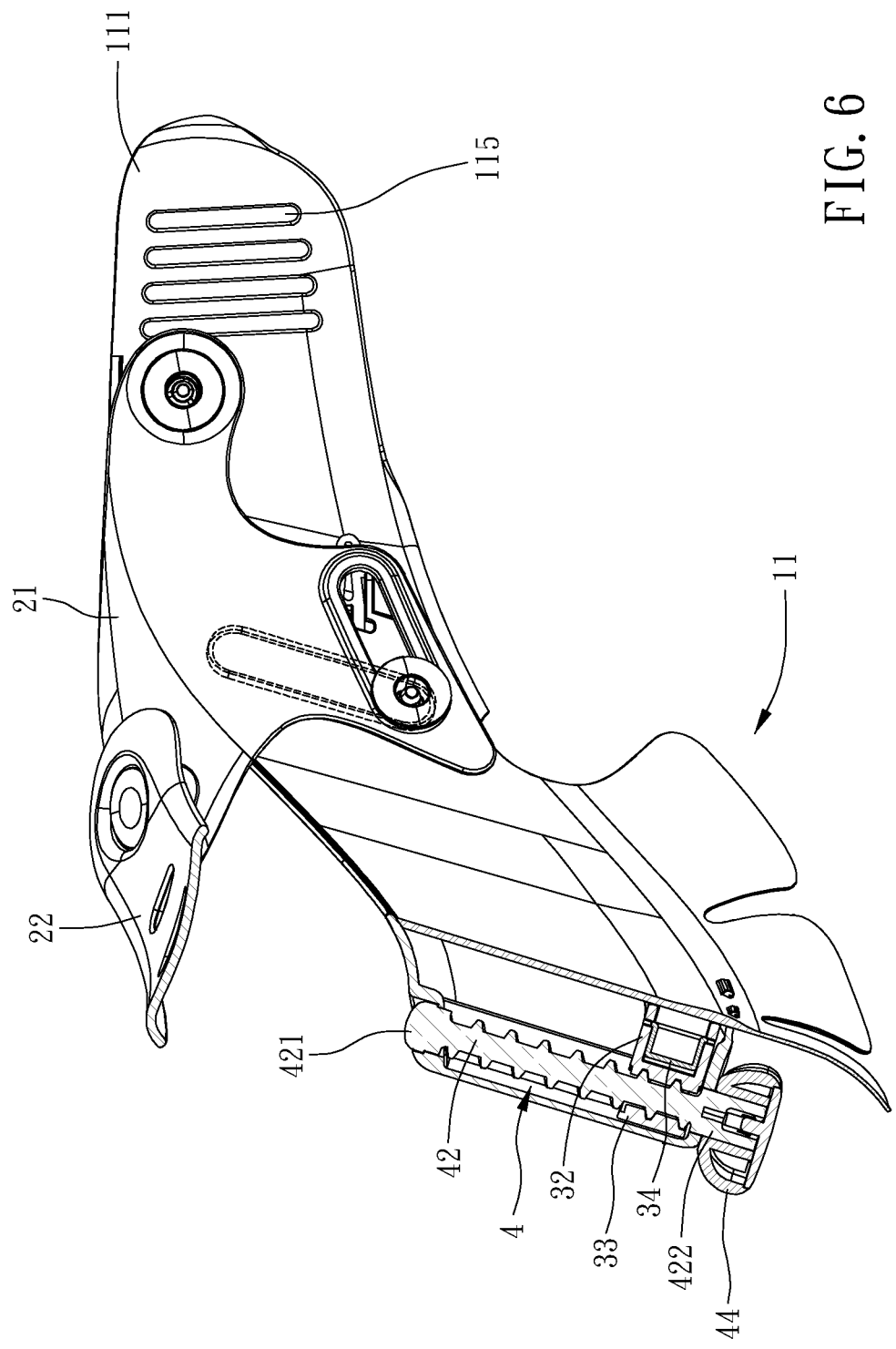
FIGS. 6 and 7 are drawings showing operation of a preferable embodiment of the present invention.
Figure 7:
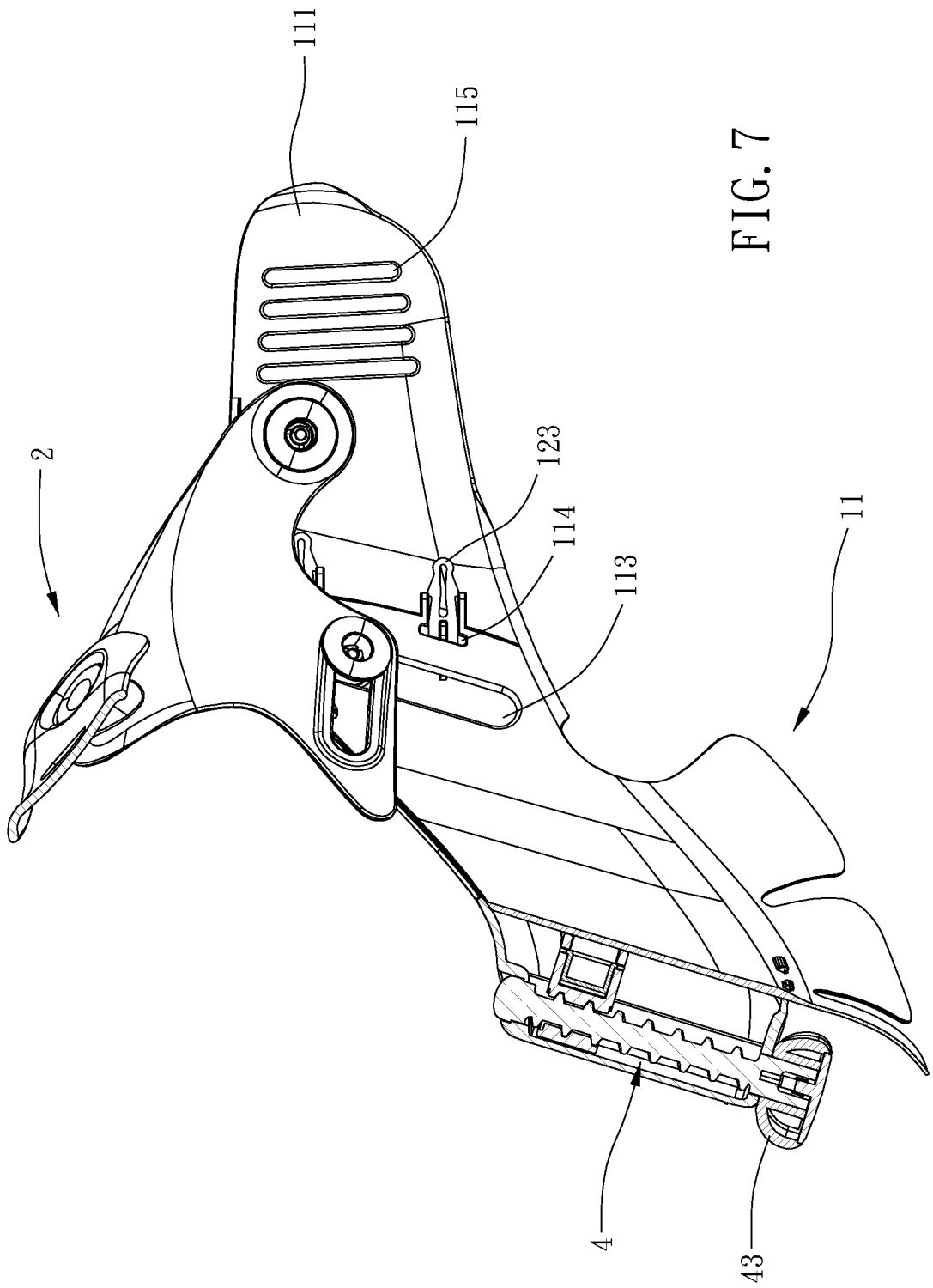
Figure 8:
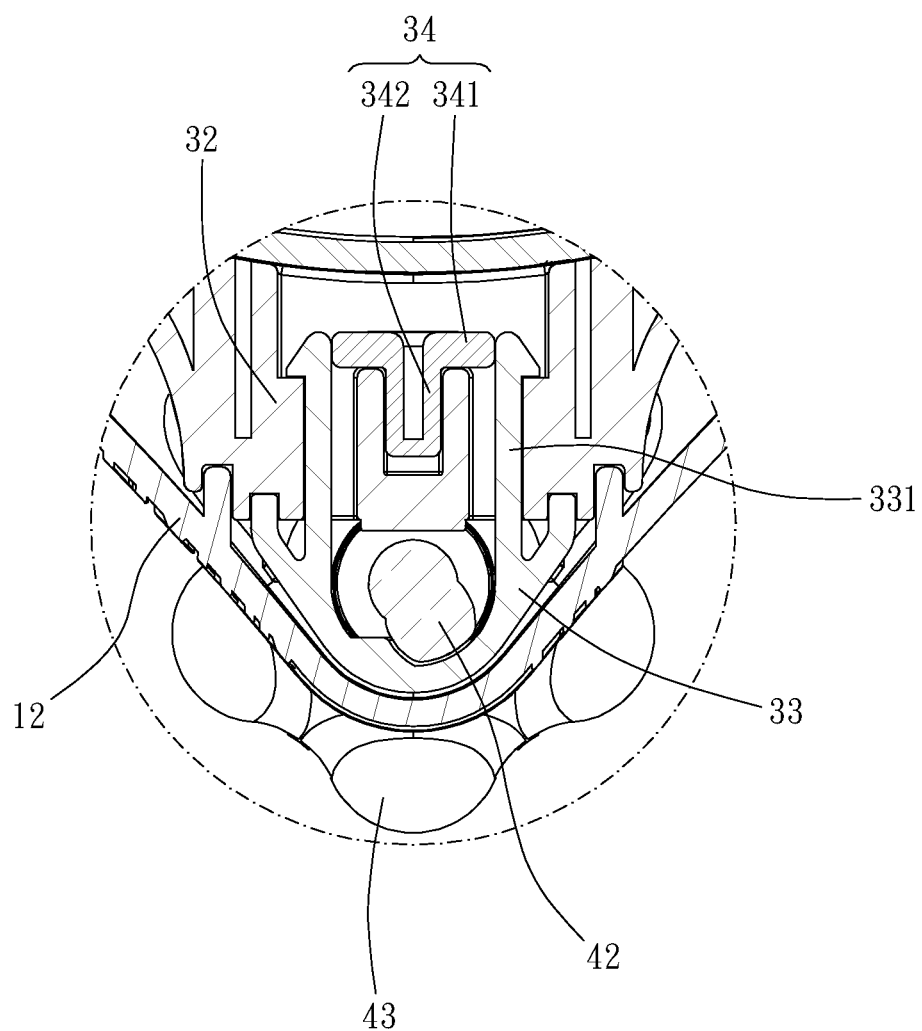
FIG. 8 is a partial cross-sectional view of a preferable embodiment of the present invention.
Figure 9:
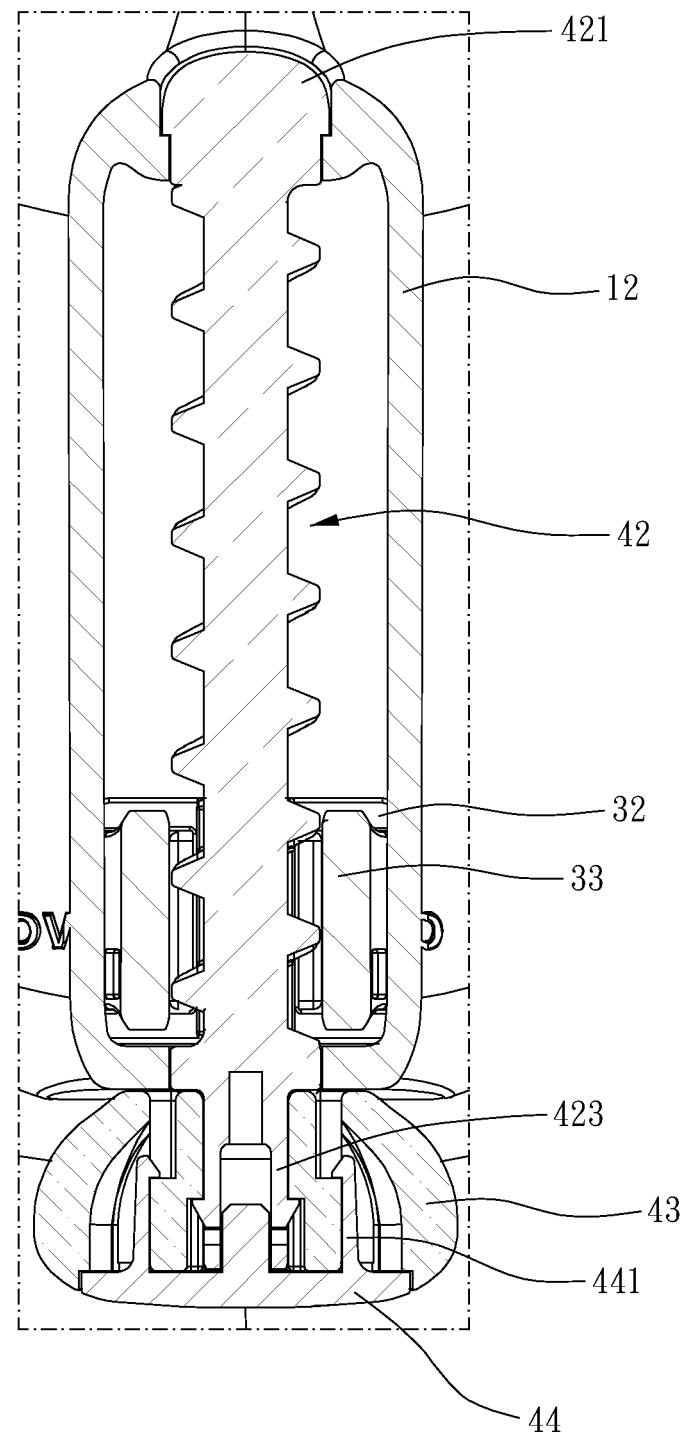
FIG. 9 is another partial cross-sectional view of a preferable embodiment of the present invention.

It needs only to rotate the knob 43 to drive the thread shaft 42 to rotate about the axial direction, and the thread shaft 42 can drive the inner thread portion 41 move in the axial direction, so that the connection member 3 and the chin support 2 having the inner thread portion 41 is able to move relative to the collar member 1 (as shown in FIGS. 6 and 7). Therefore, it is easy to operate the cervical collar, and is effective to adjust the chin support 2 relative to the collar member 1 according to various requirements; and the knob 43 is located outside an end of the collar member 1 in the axial direction, which is easy for hand operation.

Specifically, the collar member 1 includes a base 11 and a shell body 12 connected with each other, the connection member 3 is slidably disposed between the base 11 and the shell body 12, the base 11 includes two first wings 111 and a first connection portion 112, the first connection portion 112 is connected between the two first wings 111, the two first wings 111 each include a slot 113, the chin support 2 includes two swingable members 21, an end of each of the two swingable members 21 is rotatably connected with an end of one of the two first wings 111 remote from the first connection portion 112, and another end of each of the two swingable members 21 is rotatably connected with the connection member 3 and slidably disposed within the slot 113 of one of the two first wings 111. The connection member 3 moves in the axial direction to drive the two swingable members 21 to swing. In this embodiment, the chin support 2 further includes a support board 22, and the support board 22 is connected between the two swingable members 21, for supporting the chin of the user.

Specifically, the thread shaft 42 includes a head portion 421 and a non-circular section 422 at opposing ends thereof, a top portion of the shell body 12 includes a first through hole 121, a bottom portion of the shell body 12 includes a second through hole 122, the thread shaft 42 is rotatably disposed within the first through hole 121 and the second through hole 122, the head portion 421 has a diametric dimension larger than a diametric dimension of the first through hole 121 and is abutted against an outer periphery of the first through hole 121 remote from the second through hole 122, the non-circular section 422 is connected with the knob 43, and the knob 43 has a diametric dimension larger than a diametric dimension of the second through hole 122 and is abutted against an outer periphery of the second through hole 122. Through the head portion 421 and the knob 43, the thread shaft 42 is rotatable about the axial direction but is unmovable in the axial direction.

In this embodiment, two opposing sides of the non-circular section 422 each include a first hook 423, the non-circular section 422 is non-rotatably inserted to the knob 43, and the two first hooks 423 are engaged with the knob 43 to prevent the knob 43 from disengaging from the non-circular section 422. Preferably, the adjustment assembly 4 further includes a lid 44, the lid 44 includes two second hooks 441, the lid 44 is attached to a side of the knob 43 remote from the shell body 12, and the two second hooks 441 are engaged with the knob 43, for blocking dust and/foreign matters from coming into the knob 43.

The connection member 3 includes two second wings 31 and a second connection portion 32, the second connection portion 32 is connected between the two second wings 31, an end of each of the two second wings 31 remote from the second connection portion 32 is rotatably connected with an end of one of the two swingable members 21, a cover 33 is attached to the second connection portion 32, the cover 33 includes two third hooks 331, the two third hooks 331 are detachably inserted to the second connection portion 32 for securing the cover 33 to the second connection portion 32, the cover 33 and the second connection portion 32 clamp the thread shaft 42, and the inner thread portion 41 is disposed on at least one of the second connection portion 32 and the cover 33. In this embodiment, the inner thread portion 41 is disposed between the second connection portion 32 and the cover 33 so that the inner thread portion 41 and the thread shaft 42 can be well screwed with each other.

The connection member 3 further includes a blocking member 34, the blocking member 34 includes a blocking portion 341 and an insertion portion 342, the blocking portion 341 and the insertion portion 342 are connected to be a T-shaped configuration, the insertion portion 342 is inserted to the second connection portion 32, and two opposing ends of the blocking portion 341 are blocked with the two third hooks 331, respectively, which prevents the two third hooks 331 from bending and prevents the two third hooks 331 from disengaging from the second connection portion 32.

Two ends of the shell body 12 each include at least one insertion member 123, the two first wings 111 each include at least one insertion hole 114 in which the at least one insertion member is detachably inserted. In this embodiment, the two ends of the shell body 12 each include two insertion members 123, the two first wings 111 each include two insertion holes 114, and each of the two insertion members 123 is detachably inserted within one of the two insertion holes 114, so that the shell body 12 and the base 11 are detachably connected.

Preferably, an end of each of the two first wings 111 remote from the first connection portion 112 includes a plurality of grooves 115 arranged in intervals, and the plurality of grooves 115 extend in a direction lateral to a direction in which the first wing 111 extends. The plurality of grooves 115 make the end of each of the two first wings 111 remote from the first connection portion 112 easy to bend so that the collar member 1 is easy to be put on or taken off the user's neck. In this embodiment, the at least one insertion hole 114 of each of the two first wings 111 is located between the slot 113 and the plurality of grooves 115 so that the shell body 12 can cover the slot 113.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A cervical collar, including:
a collar member;
a chin support, movably disposed on the collar member;
a connection member, movably disposed on the collar member, connected with the chin support; and
an adjustment assembly, including an inner thread portion, a thread shaft and a knob, the inner thread portion being disposed on the connection member, the thread shaft being disposed on the collar member and rotatable about an axial direction, the inner thread portion and the thread shaft being screwed with each other, the knob being connected with the thread shaft on the axial direction and located outside an end of the collar member in the axial direction, wherein the thread shaft rotates to drive the inner thread portion to move in the axial direction;
wherein the collar member includes a base and a shell body connected with each other, the connection member is slidably disposed between the base and the shell body, the base includes two first wings and a first connection portion, the first connection portion is connected between the two first wings, the two first wings each include a slot, the chin support includes two swingable members, an end of each of the two swingable members is rotatably connected with an end of one of the two first wings remote from the first connection portion, another end of each of the two swingable members is rotatably connected with the connection member and slidably disposed within the slot of one of the two first wings.

2. The cervical collar of claim 1, wherein the thread shaft includes a head portion and a non-circular section at opposing ends thereof, a top portion of the shell body includes a first through hole, a bottom portion of the shell body includes a second through hole, the thread shaft is rotatably disposed within the first through hole and the second through hole, the head portion has a diametric dimension larger than a diametric dimension of the first through hole and is abutted against an outer periphery of the first through hole remote from the second through hole, the non-circular section is connected with the knob, and the knob has a diametric dimension larger than a diametric dimension of the second through hole and is abutted against an outer periphery of the second through hole.

3. The cervical collar of claim 2, wherein two opposing sides of the non-circular section each include a first hook, the non-circular section is non-rotatably inserted to the knob, and the two first hooks are engaged with the knob.

4. The cervical collar of claim 3, wherein the adjustment assembly further includes a lid, the lid includes two second hooks, the lid is attached to a side of the knob remote from the shell body, and the two second hooks are engaged with the knob.

5. The cervical collar of claim 4, wherein the connection member includes two second wings and a second connection portion, the second connection portion is connected between the two second wings, an end of each of the two second wings remote from the second connection portion is rotatably connected with an end of one of the two swingable members, a cover is attached to the second connection portion, the cover includes two third hooks, the two third hooks are detachably inserted to the second connection portion, the cover and the second connection portion clamp the thread shaft, and the inner thread portion is disposed on at least one of the second connection portion and the cover; the connection member further includes a blocking member, the blocking member includes a blocking portion and an insertion portion, the blocking portion and the insertion portion are connected to be a T-shaped configuration, the insertion portion is inserted to the second connection portion, and two opposing ends of the blocking portion are blocked with the two third hooks, respectively; two ends of the shell body each include at least one insertion member, the two first wings each include at least one insertion hole in which the insertion member is detachably inserted; an end of each of the two first wings remote from the first connection portion includes a plurality of grooves arranged in intervals, and the plurality of grooves extend in a direction lateral to a direction in which the first wing extends; the at least one insertion hole of each of the first wing is located between the slot and the plurality of grooves of one of the two first wings; the chin support further includes a support board, and the support board is connected between the two swingable members.

6. The cervical collar of claim 1, wherein the connection member includes two second wings and a second connection portion, the second connection portion is connected between the two second wings, an end of each of the two second wings remote from the second connection portion is rotatably connected with an end of one of the two swingable members, a cover is attached to the second connection portion, the cover includes two third hooks, the two third hooks are detachably inserted to the second connection portion, the cover and the second connection portion clamp the thread shaft, and the inner thread portion is disposed on at least one of the second connection portion and the cover.

7. The cervical collar of claim 6, wherein the connection member further includes a blocking member, the blocking member includes a blocking portion and an insertion portion, the blocking portion and the insertion portion are connected to be a T-shaped configuration, the insertion portion is inserted to the second connection portion, and two opposing ends of the blocking portion are blocked with the two third hooks, respectively.

8. The cervical collar of claim 1, wherein two ends of the shell body each include at least one insertion member, the two first wings each include at least one insertion hole in which the at least one insertion member is detachably inserted.

9. The cervical collar of claim 1, wherein an end of each of the two first wings remote from the first connection portion includes a plurality of grooves arranged in intervals, and the plurality of grooves extend in a direction lateral to a direction in which the first wing extends.

\* \* \* \* \*